(12) United States Patent
Brueggemeier et al.

(10) Patent No.: US 7,105,542 B2
(45) Date of Patent: Sep. 12, 2006

(54) 2-HETEROSUBSTITUTED 3-ARYL-4H-1-BENZOPYRAN-4-ONES AS NOVEL THERAPEUTICS IN BREAST CANCER

(75) Inventors: Robert W. Brueggemeier, Dublin, OH (US); Young-Woo Kim, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 10/634,463

(22) Filed: Aug. 4, 2003

(65) Prior Publication Data

US 2004/0087586 A1    May 6, 2004

Related U.S. Application Data

(60) Provisional application No. 60/400,742, filed on Aug. 2, 2002.

(51) Int. Cl.
*A61K 31/445* (2006.01)
*C07D 405/10* (2006.01)

(52) U.S. Cl. ....................... 514/320; 546/196
(58) Field of Classification Search ............... 514/320; 546/196
See application file for complete search history.

(56) References Cited

U.S. PATENT DOCUMENTS

| | | | | |
|---|---|---|---|---|
| 4,960,908 A | * | 10/1990 | Ito et al. ................ | 549/403 |
| 5,420,307 A | | 5/1995 | Hagen et al. | |
| 5,948,808 A | | 9/1999 | Safe | |
| 6,150,395 A | | 11/2000 | Firestone et al. | |
| 6,620,838 B1 | * | 9/2003 | McKie et al. ........... | 514/422 |

FOREIGN PATENT DOCUMENTS

| | | | |
|---|---|---|---|
| WO | WO95//10513 | * | 4/1995 |
| WO | WO 98/29403 | * | 7/1998 |

OTHER PUBLICATIONS

Jadhav et al. "Synthesis of 2-aryl . . . " CA 99:522236 (1983).*
Saxena et al. "Flavones and coumarins . . . " CA 126:1217 (1996).*
Kim et al. "Synthesis and estrogen receptor binding . . . " CA 139:117307 (2003).*
Grever et al. "The NCI cancer drug discovery . . . " Seminars in oncology, v. 19, p. 622-629 (1992).*
King et al. "Medicinal chemistry ;principles and practice" p. 206-209 (1994).*
Kim, Young-Woo et al., "Synthesis and Estrogen Receptor Binding Affinities of 7-Hydrxy-3-(4-hydroxyphenyl)-4H-1-benzopyran-4-ones Containing a Basic Side Chain," Science Direct, Bioorganic & Medicinal Chemistry Letters 13 (2003) 1475-1478.
Kim, Young-Woo et al., "Novel 2-arylthiolsoflavones as potential therapeutic agents for homorne-dependent breast cancer," Nat'L American Chemical Society Meeting, Aug. 18-22, 2002 In Boston, MA.
International Search Report from corresponding appln. No. PCT/US03/24520, Jun. 21, 2004.

* cited by examiner

*Primary Examiner*—Celia Chang
(74) *Attorney, Agent, or Firm*—Calfee, Halter & Griswold LLP

(57) ABSTRACT

The present invention provides 2-heterosubstituted 3-aryl-4H-benzopyran-4-one compounds for the treatment of cancers, namely breast cancer. This invention further provides a method of synthesis of 2-(alkylthio)isoflavones that can be carried out at ambient conditions. This invention further provides a method of synthesis of the 2-heterosubstituted 3-aryl-4H-benzopyran-4-one from a 2-(alkylthio)isoflavone. The invention further provides methods of using the 2-heterosubstituted 3-aryl-4H-benzopyran-4-one compounds for the treatment of breast cancer in mammals.

20 Claims, 9 Drawing Sheets

Scheme 1

Scheme 2

Scheme 3. Reagents: (a) resorcinol, BF$_3$-OEt$_2$, 100°C, 2h; (b) PPh$_3$, DIAD, MeOH, THF, rt, 5 min.; (c) CS$_2$, R$_2$X, n-Bu$_4$N•HSO$_4$, aq. NaOH, THF, rt, 3-7 h.

6a

A | fast

7

B | slow

2a (87%)

Scheme 4. Reagents: CS$_2$, R$_2$X, $n$-Bu$_4$N•HSO$_4$, aq. NaOH, THF, rt, 3 h.

Scheme 5. Reagents: $CS_2$, $R_2X$, $n$-$Bu_4N·HSO_4$, aq. NaOH, THF, rt, 3-7 h.

Dose Response Studies in MCF-7 Cells

Dose Response Studies in MCF-7 Cells

Screening Data for Isoflavone Library in MDA-MB-231 (ER-) Cells

2-HETEROSUBSTITUTED 3-ARYL-4H-1-BENZOPYRAN-4-ONES AS NOVEL THERAPEUTICS IN BREAST CANCER

CROSS-REFERENCE TO RELATED APPLICATIONS

This application claims priority to U.S. Provisional Patent Application No. 60/400,742, filed Aug. 2, 2002, the entirety of which is incorporated herein by reference.

STATEMENT ON FEDERALLY FUNDED RESEARCH

This work was supported, at least in part, by grants DMAD 17-00-1-0388 and DMAD 17-99-1-9342 from the USAMRMC Breast Cancer Program. The government has certain rights in this invention.

FIELD OF THE INVENTION

The present invention relates to compounds, particularly 2-heterosubstituted 3-aryl-4H-benzopyran-4-ones, for treating or preventing cancer in a mammalian subject and methods of making and using such 2-heterosubstituted 3-aryl-4H-benzopyran-4-ones.

BACKGROUND OF THE INVENTION

Breast cancer kills thousands of women annually. While surgical intervention has saved the lives of many women, radical and partial mastectomies often prove physically and emotionally debilitating. Moreover, patients who have undergone surgery and subsequent chemotherapy often experience recurrence.

The 4H-1-benzopyran-4-one ring system is widely found in a number of natural products such as flavonoids. These natural products have demonstrated numerous biological activities such as antiviral, anti-inflammatory, antiallergic, antimutagenic and anticarcinogenic activities.[1] Genistein, an isoflavonoid, for example, has been known to act as an antagonist on the estrogen receptor suppressing the development of hormone-dependent breast cancer.

This fact has led us to investigate novel 4H-1-benzopyran-4-one derivatives as new therapeutic agents for hormone-dependent breast cancer.[2] As part of this effort, we have been interested in 3-aryl-2-alkylthio-4H-1-benzopyran-4-ones, or 2-(alkylthio)isoflavones, as potential drug candidates in this area. However, only a few methods have been reported for the synthesis of 2-alkylthio-4H-1-benzopyran-4-ones.[3] Furthermore, these methods suffer several disadvantages such as low yields, multiple steps, and harsh conditions. Recently, a high yielding one-pot synthesis of 2-methylthio-4H-1-benzopyranones has been reported using KHMDS as a base.[4] However, this method also requires skillful handling of the base, low temperature, and anhydrous reaction conditions. A convenient method of synthesis of 2-alkylthio-4H-1-benzopyran-4-ones or 2-(alkylthio) isoflavones would provide a convenient starting point for the development of new therapeutics for the treatment of breast cancer.

Accordingly, it is desirable to have new compounds and methods for the treatment of hormone dependent breast cancer, as well as other cancers. It is also desirable to have new, efficient, methods for the syntheses of these new compounds. It is particularly desirable that these new synthetic methods have few steps, improved yields, and mild conditions.

SUMMARY OF THE INVENTION

Figure 1:
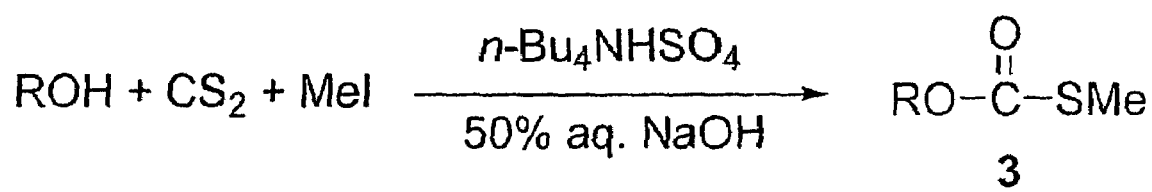
FIG. 1 shows a phase transfer catalyst procedure for the synthesis of O-alkyl-S-methyl dithiocarbonates and a cyclization of the O-alkyl-S-methyl dithiocarbonates to generate the 2-(alkylthio)isoflavones in a single step.
Figure 1:
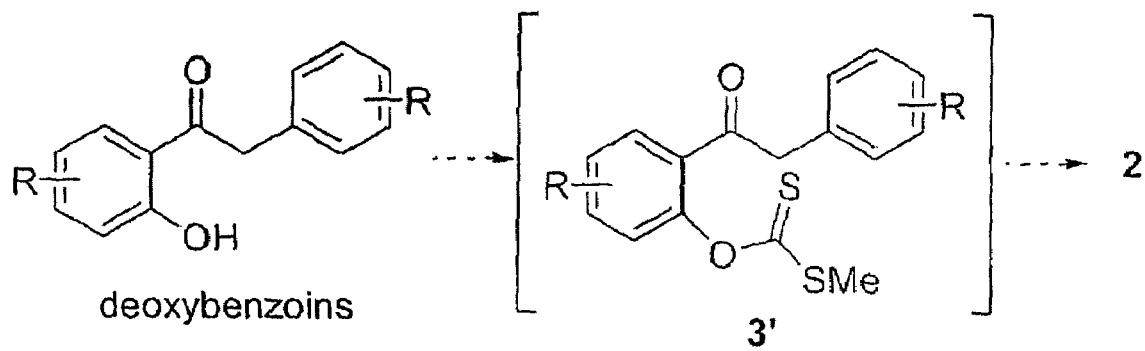

In one aspect, the present invention provides compounds for treating or preventing cancer, particularly breast cancer in a subject. The compounds are new 2-heterosubstituted 3-aryl-4H-1-benzopyran-4-ones and pharmaceutical compositions that contain one of more of the 2-heterosubstituted 3-aryl-4H-1-benzopyran-4-ones of the present invention and derivatives thereof. The 2-heterosubstituted 3-aryl-4H-1-benzopyran-4-ones have structure A:

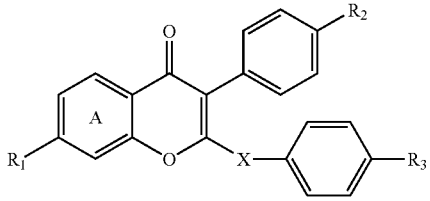

wherein
X is selected from the group consisting of O, N, S, SO, and $SO_2$;
$R_1$ and $R_2$ can be the same or different and are selected from the group consisting of H, OH, $OCH_3$, $OCH_2CH_3$, $OCH_2C_6H_5$, $NH_2$, $NHCH_3$, $N(CH_3)_2$, $CH_3$, $CH_2CH_3$, $CH_2CH_2CH_3$, $CH(CH_3)_2$, $C(CH_3)_3$, $NO_2$, F, Cl, Br, $CF_3$, SH, $SCH_3$, $SCH_2CH_3$, OCOCH3, $OCOC(CH_3)_3$, $OCOCH_2COOH$, and CN;
$R_3$ is selected from the group consisting of H, OH, $OCH_3$, $OCH_2CH_3$, $NH_2$, $NHCH_3$, $N(CH_3)_2$, $NO_2$, $CH_3$, $CH_2CH_3$, $CH_2CH_2CH_3$, $CH(CH_3)_2$, $C(CH_3)_3$, F, Cl, Br, $CF_3$, SH, $SCH_3$, $SCH_2CH_3$, CN,

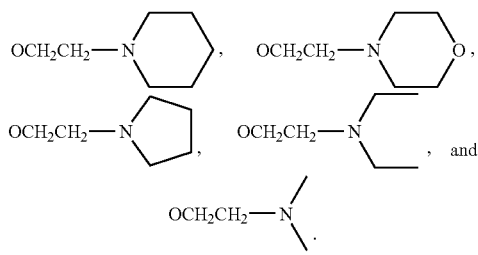

An especially preferred subclass of compounds are those of structure A wherein X is selected from S and O; $R_1$ is selected from OH and $OC_6H_5$; $R_2$ is selected from OH and $OCH_3$; and $R_3$ is selected from OH and 2-(1-piperidinyl) ethoxy.

In another aspect, the present invention provides a one-pot method of making 2-(alkylthio)isoflavones. The method of synthesizing the 2-(alkylthio)isoflavones comprises selecting a deoxybenzoin compound, preparing a mixture of the deoxybenzoin compound, carbon disulfide, alkyl halide, and tetrabutylammonium hydrogensulfate. While the mixture is stirred, aqueous sodium hydroxide is added to the mixture. The resulting mixture is allowed to stir until the reaction is complete, from about 3 to about 7 hours, at room temperature. Optionally, the deoxybenzoin starting compound can be prepared by a Freidel-Crafts acylation of resorcinal with arylacetic acids followed by Mitsunobu reaction. The resulting 2-(alkylthio)isoflavone can be filtered and purified, if desired.

In another aspect of the present invention, the 2-(alkylthio)isoflavone can then be used to prepare a 2-heterosubstituted 3-aryl-4H-benzopyran-4-one. The method comprises (a) selecting a 2-(alkylthio)isoflavone; (b) optionally protecting reactive groups on the 2-(alkylthio)isoflavone; (c) oxidizing the alkylthio group to an alkylsulfonyl group; and (d) substituting the alkylsulfonyl group with a heteroalkyl or heteroaryl group to form a 2-heterosubstituted 3-aryl-4H-benzopyran-4-one. Preferably the oxidation step is carried out with mCPBA in a polar, aprotic solvent, such as $CH_2Cl_2$. The method further comprises the addition of drug-like substituents, such as 1-piperidineylethoxy groups, on the 2-heteroaryl 3-aryl-4H-benzopyran-4-ones. The method further comprises the step of deprotecting the 2-heteroaryl 3-aryl-4H-benzopyran-4-one compound. The method optionally further comprises a purification step.

In still another aspect of the present invention, a method of using the compounds of formula A in the treatment of breast cancer, particularly, but not limited to hormone-dependent breast cancer. The method comprises administering a therapeutically effective amount of a 2-heterosubstituted 3-aryl-4H-1-benzopyran-4-one compound of structure A to a subject in need of treatment. The 2-heterosubstituted 3-aryl-4H-1-benzopyran-4-one compound can be administered in accordance with conventional methods, and in doses similar to drugs currently available for the treatment of breast cancer. The 2-heterosubstituted 3-aryl-4H-1-benzopyran-4-one compounds of present invention may also be used as part of a combination therapy. The invention further provides a method for the prevention of breast cancer in subjects who are susceptible to developing breast cancer, comprising administering a therapeutically effective amount of a compound of structure A.

DETAILED DESCRIPTION OF THE INVENTION

The benzopyranone ring system is widely distributed in a number of natural products, including flavonoids. Compounds in this class have shown a range of important biological and medicinal activities. We have investigated a series of 2-alkyl substituted benzopyranone analogs to identify potential drug candidates for hormone-dependent breast cancer. In the course of this study, we have also prepared heteroalkyl and heteroaryl benzopyranone analogs.

Our synthetic strategy for the construction of the 2-alkylthiobenzopyranon-4-ones involves the simultaneous intramolecular cyclization of alpha-oxoketene dithioacetals derived from deoxybenzoins as a key step under the TBS deprotonation condition. The alkylthio ether group at the 2 position can also serve as a good leaving group to introduce other alkylated heteroatoms such as alkyl or aryl amines. This synthetic strategy is especially useful for solid-phase combinatorial synthesis of medicinal agents for molecular targets in hormone-dependent breast cancer.

The present invention provides 2-heterosubstituted 3-aryl-4H-benzopyran-4-one compounds useful for the prevention and treatment of cancers, particularly but not limited to breast cancers, as well as methods of using these compounds to treat breast cancers in subjects in need of such treatment. The method involves treating the subject in need of such treatment with a therapeutically effective amount of a 2-heterosubstituted 3-aryl-4H-benzopyran-4-one compound of the present invention or a derivative or pharmaceutically acceptable salt thereof. The present invention also provides methods of making the 2-heterosubstituted 3-aryl-4H-benzopyran-4-one compounds.

The 2-heterosubstituted 3-aryl-4H-benzopyran-4-one compounds and methods of the present invention are useful for, but not limited to treating, inhibiting, or delaying the onset of cancers. The 2-heterosubstituted 3-aryl-4H-benzopyran-4-one compounds of the present invention are also useful in the treatment of precancers. The compounds and methods are useful for treating cancers including, but not limited to, breast cancer, leukemia, non-small cell lung cancer, colon cancer, CNS cancer, melanoma, ovarian cancer, renal cancer, prostate cancer, bladder cancer, and lymphoma. Furthermore, they are useful in the prevention of these cancers in individuals with precancers, as well as individuals prone to these disorders.

By "treating" is meant curing, ameliorating or tempering the severity of the cancer or the symptoms associated therewith. The terms "treating," "treatment," and "therapy" as used herein refer to curative therapy, prophylactic therapy, and preventative therapy.

"Preventing" or "prevention" means preventing the occurrence of the cancer, or tempering the severity of the cancer if it is develops subsequent to the administration of the instant compositions. This preventing the onset of a clinically evident unwanted cell proliferation altogether or preventing the onset of a preclinically evident stage of unwanted rapid cell proliferation in individuals at risk. Also intended to be encompassed by this definition is the prevention of metastatis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject having a neoplasia, such as cancer or precancer. For methods of prevention the subject is any human or animal subject, and preferably is a human subject who is at risk of developing a cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

The term "derivative" is intended to encompass compounds which are structurally related to the present invention or which possess the substantially equivalent activity to the parent 2-heterosubstituted 3-aryl-4H-benzopyran-4-one compounds, as measured by the derivative's ability to inhibit activity in an in vitro estrogen dependent cell proliferation assay using human breast cells (MCF-7). By way of example, such compounds may include, but are not limited to, prodrugs thereof. Such compounds can be formed in vivo, such as by metabolic mechanisms.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes radicals selected from F, Cl, Br, and I.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl on so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth.

The agents of the present invention may be administered orally, intravenously, intranasally, rectally, or by any means which delivers an effective amount of the active agent to the tissue or site to be treated. It will be appreciated that different dosages may be required for treating different disorders. An effective amount of an agent is that amount which causes a statistically significant decrease in neoplastic cell count, growth, or size. Neoplastic disorders responsive to the agents of the present invention include, but are not limited to, breast cancer.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

The active agents may be administered along with a pharmaceutical carrier and/or diluent. The agents of the present invention may also be administered in combination with other agents, for example, in association with other chemotherapeutic or immunostimulating drugs or therapeutic agents. Examples of pharmaceutical carriers or diluents useful in the present invention include any physiological buffered medium, i.e., about pH 7.0 to 7.4 comprising a suitable water soluble organic carrier. Suitable water soluble organic carriers include, but are not limited to corn oil, dimethylsulfoxide, gelatin capsules, etc.

Also included in the family of 2-heterosubstituted 3-aryl-4H-benzopyran-4-one compounds are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable.

Suitable pharmaceutically acceptable acid addition salts of 2-heterosubstituted 3-aryl-4H-benzopyran-4-one compounds may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids.

Suitable pharmaceutically acceptable base addition salts of 2-heterosubstituted 3-aryl-4H-benzopyran-4-one compounds include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the 2-heterosubstituted 3-aryl-4H-benzopyran-4-one compounds. All of these salts may be prepared by conventional means from the corresponding 2-heterosubstituted 3-aryl-4H-benzopyran-4-one compounds by reacting, for example, the appropriate acid or base with the 2-heterosubstituted 3-aryl-4H-benzopyran-4-one compound.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

There are large numbers of antineoplastic agents available in commercial use, in clinical evaluation and in pre-clinical development, which could be selected for treatment of cancers or other neoplasias by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors may be used. Suitable agents which may be used in combination therapy will be recognized by those of skill in the art.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Synthetic Methods Several years ago a phase transfer catalysis procedure was reported for the synthesis of O-alkyl-S-methyl dithiocarbonates (3) in high yields (FIG. 1, Scheme 1).[5] We investigated this procedure for the synthesis of 2-(alkylthio)isoflavones (2) from deoxybenzoins. The purpose of our study was to determine whether the O-aryl-S-alkyl dithiocarbonates 3' would undergo further cyclization reaction in this reaction condition, thereby directly generating the desired 2-(alkylthio)isoflavones 2 in a single step (FIG. 1, Scheme 2).

EXAMPLE 1

General Experimental Procedure for Preparing 2-(alkylthio)isoflavones

To a stirred mixture of a deoxybenzoin (1 mmol), carbon disulfide (0.6 mL, 10 mmol), alkyl halide (2.2 mmol), and tetrabutylammonium hydrogensulfate (34 mg, 0.1 mmol) in THF (3 mL) and water (1 mL) was slowly added aqueous NaOH solution (1.2 mL, 12 mmol, 10 M) at room temperature. A slight exothermic reaction and a color change of the mixture were observed. The resulting mixture was vigorously stirred at room temperature for several hours, and the product was extracted with ethyl acetate (2×10 mL). The separated organics were washed with water (10 mL) and then with brine (10 mL), dried over MgSO$_4$, and filtered. The filtrate was concentrated under reduced pressure, and the residue was purified by silica gel column chromatography (eluting with EtOAc/hexane or MeOH/CHCl$_3$) to give the product as a white solid. All the products were recrystallized from EtOAc/hexane.[9]

EXAMPLE 2

Preparation of the Deoxybenzoins

Figure 2:
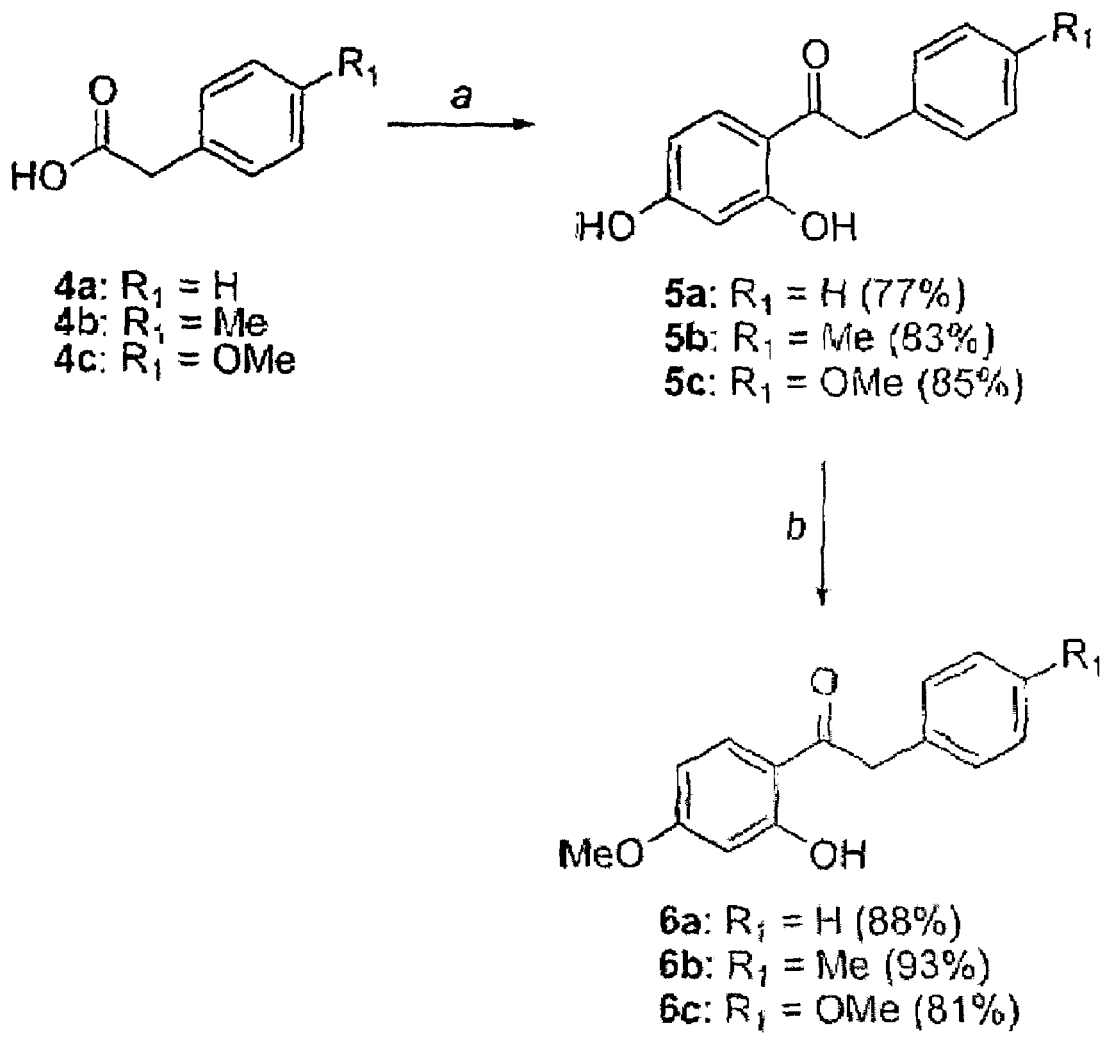
FIG. 2 shows the synthetic scheme for preparation of deoxybenzoins by Friedel-Crafts acylation of resorcinol with corresponding arylacetic acids followed by Mitsunobu reaction for the selective methylation of 4-hydroxyl group.

Deoxybenzoins 6 were prepared by Friedel-Crafts acylation of resorcinol with corresponding arylacetic acids followed by Mitsunobu reaction for the selective methylation of 4-hydroxyl group (FIG. 2, Scheme 3).[6]

Figure 3:
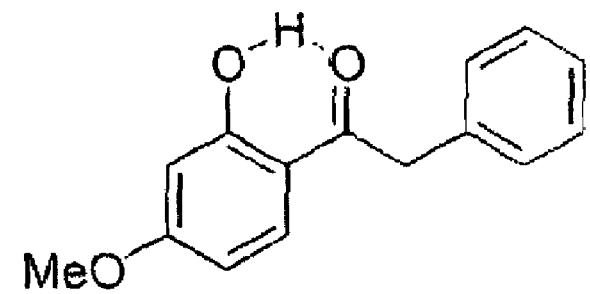
FIG. 3 shows the production of a 2-(methylthio)isoflavone from the deoxybenzoin.
Figure 3:
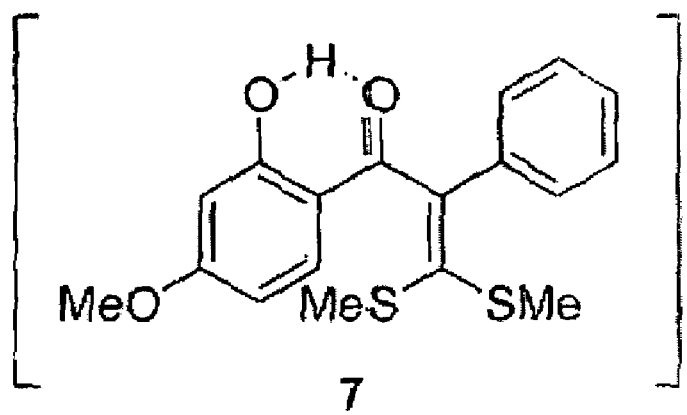
Figure 3:
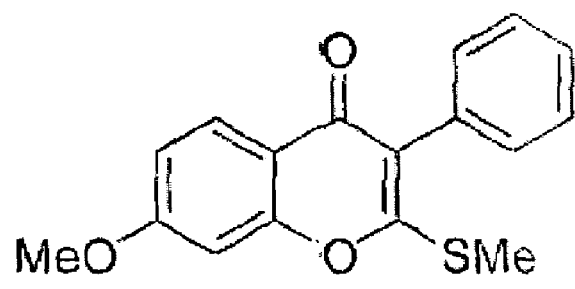

When the deoxybenzoin 6a, carbon disulfide, and methyl iodide in a THF[7]-water two-phase system were treated with aqueous NaOH solution at room temperature in the presence of 10 mole % of tetrabutylammonium hydrogensulfate (n-Bu$_4$N.HSO$_4$), the desired 2-(methylthio)isoflavone 2a was obtained in 87% yield (FIG. 3, Scheme 4). The reaction apparently occurred in a stepwise manner as monitored by TLC. Interestingly, the spectral data of the intermediate indicated that the reaction proceeded not via the O-alkyl-S-methyl dithiocarbonate but via α-oxoketene dithioacetal (7).[8] This could be explained by the intramolecular hydrogen bond of the starting deoxybenzoin, which might facilitate the enolate formation. In addition, the formation of α-oxoketene dithioacetal intermediate (FIG. 3, step A, Scheme 4) is very fast; all the starting material was converted into the intermediate as soon as the aqueous NaOH solution was added. However, when the reaction is done at 0° C., intermediate 7 can be obtained within 5 min in a high yield (>90%). In contrast, the subsequent cyclization (FIG. 3, step B, Scheme 4) is the rate-determining step, and thereby requires a longer reaction time (3–4 h) to be completed presumably because the intramolecular hydrogen bond of intermediate 7 is still rigid. However, this reaction can be completed within an hour when the reaction mixture is warmed at ~50° C.

Figure 4:
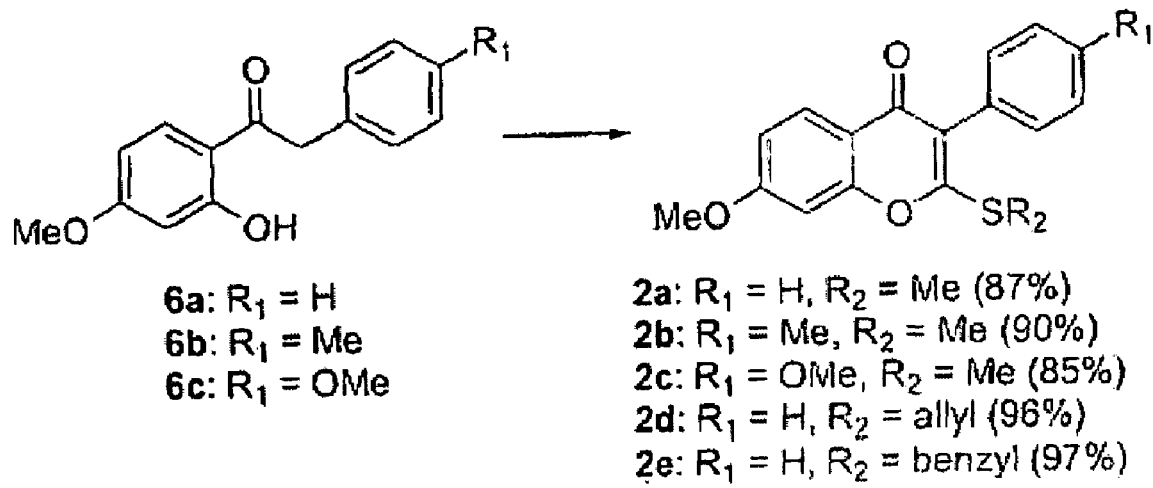
FIG. 4 shows the production of five additional 2-(methylthio)isoflavone from three deoxybenzoins.

Similar results were obtained when deoxybenzoin 6b and 6c were used as starting materials (FIG. 4, Scheme 5). Therefore, this method proved to be efficient to prepare the 2-(methylthio)isoflavones, which can be used as useful intermediates to introduce various nucleophiles at the 2-position. In addition, as shown in Scheme 5 (FIG. 4), this process was also efficient when different alkyl halides were used as an alkylating agent, indicating diverse alkylthio groups can be directly introduced at the 2-position using this process.

In summary, we have described a convenient phase transfer catalysis procedure allowing the efficient conversion of deoxybenzoins into 2-(alkylthio)isoflavones in a single step at the ambient reaction condition. This method can be very useful to generate a number of drug-like compounds from easily available deoxybenzoins in a short period of time.

EXAMPLE 3

Preparation of the 2-heterosubstituted 3-aryl-4H-1-benzopyran-4-ones

The 2-heterosubstituted 3-aryl-4H-1-benzopyran-4-one compounds are formed from the 2-(alkylthio)isoflavones of Example 1 by the addition of a side chain as the 2-position through oxidation then substitution of the methylthio group. Reflux of the 2-(alkylthio)isoflavone with mCPBA in $CH_2Cl_2$ for approximately one hour resulted in the oxidation of the starting 2-(alkylthio)isoflavone compound. The substitution at the 2-position was achieved by mixing the oxidized 2-(alkylthio)isoflavone with p-sulfhydrylphenol, and sodium hydride in DMF for 15 minutes at room temperature. Then, the 2-substituent of the resulting compound was converted to a 4-[2-(1-piperidinyl)ethoxy]thiophenoxy group by reacting with of 2-piperidinylchloroethane and HCl in $Cs_2CO_3$, DMF for 8 hours at room temperature to form the end product. Subsequent deprotection was carried out with $BBr_3$, less than 2 eq. $CH_2Cl_2$ to yield hydroxyl groups at the $R_1$ and $R_2$ positions. Alternatively, $BF_3OEt_2$ and $Me_2S$, both in excess in $CH_2Cl_2$ was used to give hydroxyl groups at the $R_1$, $R_2$, and $R_3$ positions.

EXAMPLE 4

Several members of the combinatorial library that was prepared in accordance with the methods of this invention have been tested for effects on proliferation in MCF-7 cells and MDA-MB-231 cells. The results are shown in Table 1.

EXAMPLE 6

$IC_{50}$ ranges for several members of the combinatorial library were determined within 95% confidence intervals. The results are shown in Table 2, below.

TABLE 2

| Compound # | $IC_{50}$ Range | $IC_{50} \pm \Delta IC_{50}$ (μM) | $IC_{50}$ (μM) (From Program) | $R^2$ |
|---|---|---|---|---|
| 174 | — | — | — | — |
| 234 | 0.36–0.92 | 0.64 ± 0.28 | 0.58 | .904 |
| 244 | 7.86–15.74 | 11.80 ± 3.94 | 11.12 | .916 |
| 260 | — | — | — | — |
| 262 | — | — | — | — |
| 220 | 2.87–7.68 | 5.28 ± 2.40 | 4.70 | .955 |
| 230 | 2.41–7.23 | 4.82 ± 2.41 | 4.17 | .940 |
| 246 | — | — | — | — |
| 258 | 2.30–5.88 | 4.09 ± 1.79 | 3.67 | .900 |
| 268 | — | — | — | — |
| YWK-II-14 4-OH | 6.31* | 6.31* | 6.31* | .994 |
| Tamoxifen | 3.61–4.93 | 4.27 ± 0.66 | 4.22 | .993 |

—= Compounds that did not inhibit 50%, even at high concentrations;
*= The value is an estimation due to problems analyzing the data using GraphPad Prism

EXAMPLE 7

Screening assays were done with the compounds from the combinatorial library in MC-7 (ER+) Cells in the presence

TABLE 1

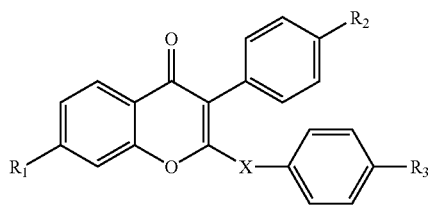

| Compound | X | $R_1$ | $R_2$ | $R_3$ | M.F. | M.W. |
|---|---|---|---|---|---|---|
| YWK-I-220 | S | OBn | OMe | OH | $C_{29}H_{22}O_5S$ | 482.55 |
| YWK-I-244 | S | OH | OH | OH | $C_{21}H_{14}O_5S$ | 378.40 |
| YWK-I-230 | S | OBn | OMe | 2-(1-piperidinyl)ethoxy | $C_{36}H_{35}NO_5S$ HCl | 630.19 |
| YWK-I-260 | S | OH | OH | 2-(1-piperidinyl)ethoxy | $C_{28}H_{27}NO_5S$ | 489.58 |
| YWK-I-234 | S | OH | OMe | 2-(1-piperidinyl)ethoxy | $C_{29}H_{29}NO_5S$ | 503.61 |
| YWK-I-246 | O | OBn | OMe | OH | $C_{29}H_{22}O_6$ | 466.48 |
| YWK-I-268 | O | OH | OH | OH | $C_{21}H_{14}O_6$ | 362.33 |
| YWK-I-258 | O | OBn | OMe | 2-(1-piperidinyl)ethoxy | $C_{36}H_{35}NO_6HCl$ | 614.13 |
| YWK-I-262 | O | OH | OH | 2-(1-piperidinyl)ethoxy | $C_{28}H_{27}NO_6$ | 473.52 |
| YWK-II-14 | O | OH | OMe | 2-(1-piperidinyl)ethoxy | $C_{29}H_{29}NO_6$ | 487.54 |

EXAMPLE 5

Figure 5:
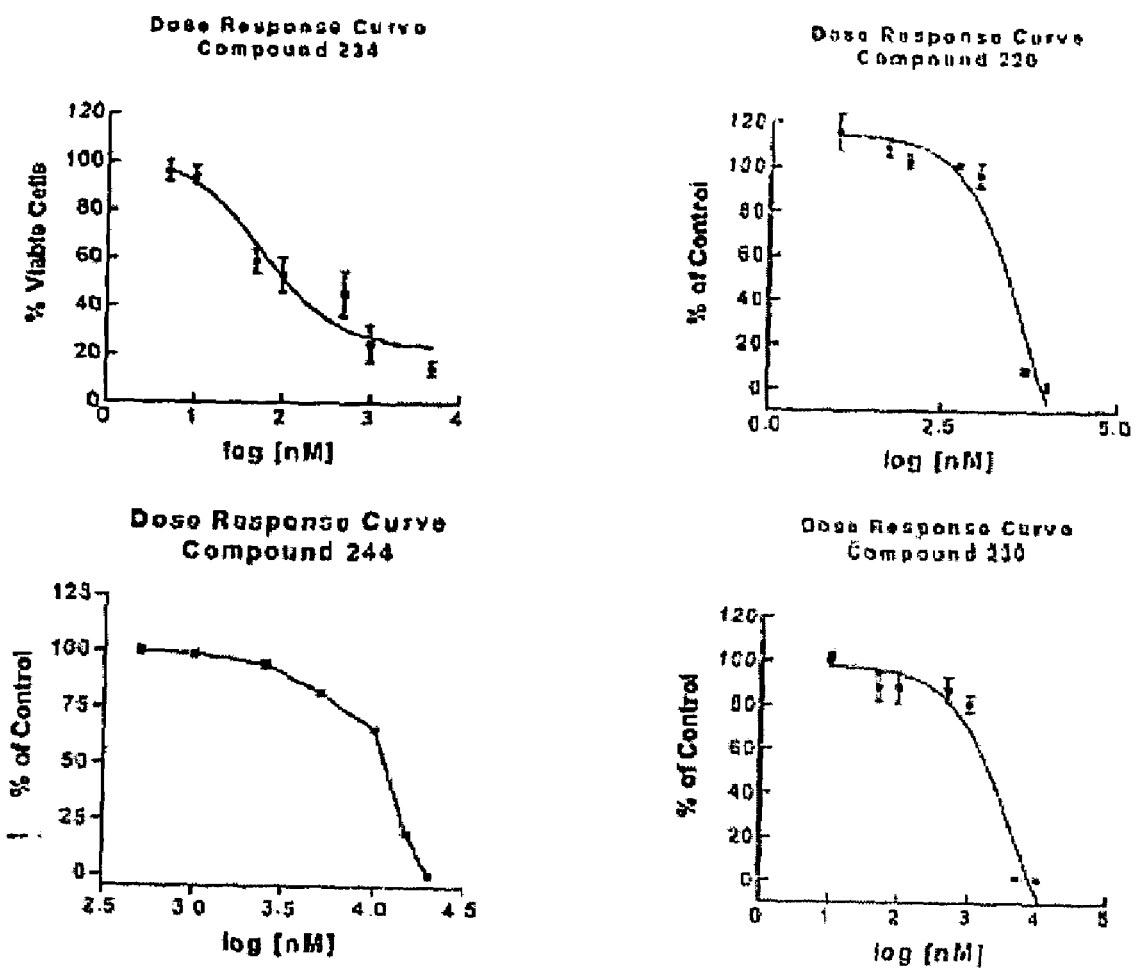
FIG. 5 shows dose response studies in MCF-7 cells for compounds 234, 220, 244, and 230.
Figure 6:
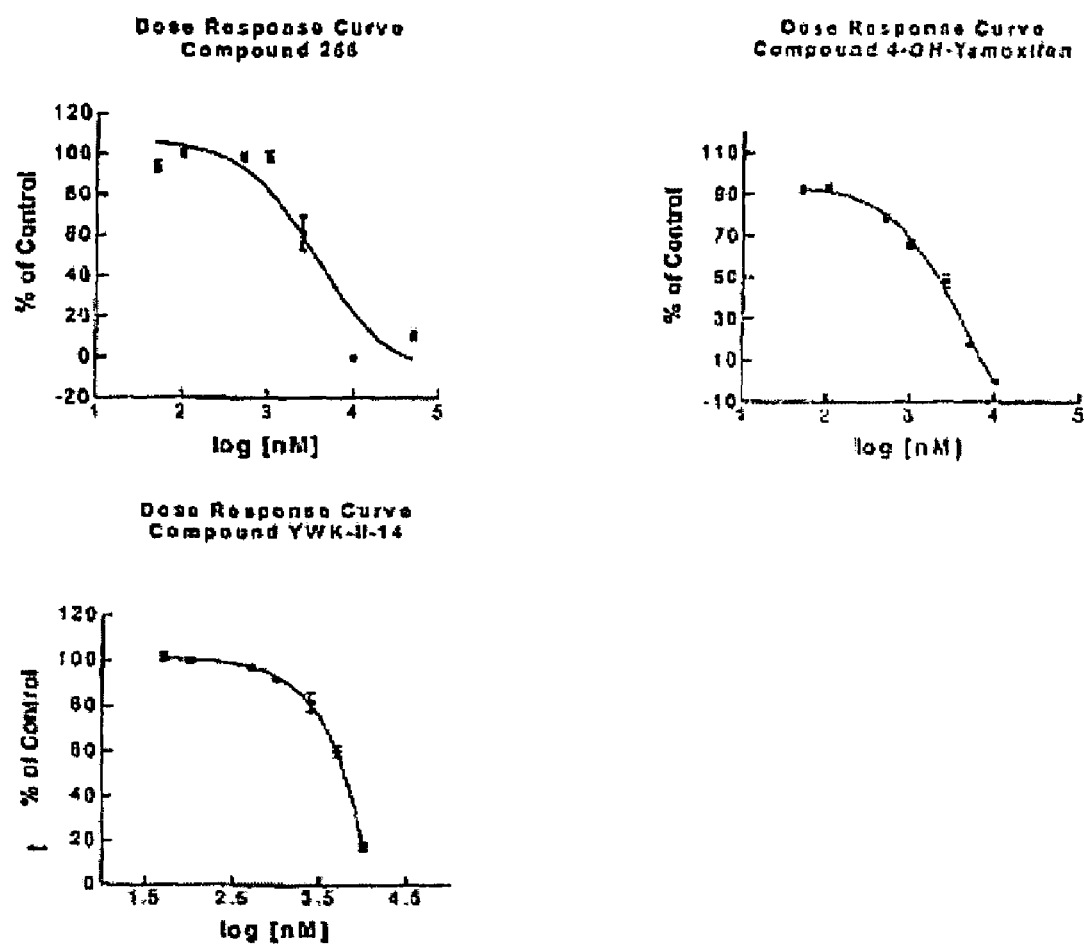
FIG. 6 shows dose responsive studies in MCF-7 cells for compounds 258, YWK-II-14, and 4-OH Tamoxifen.
Figure 7:
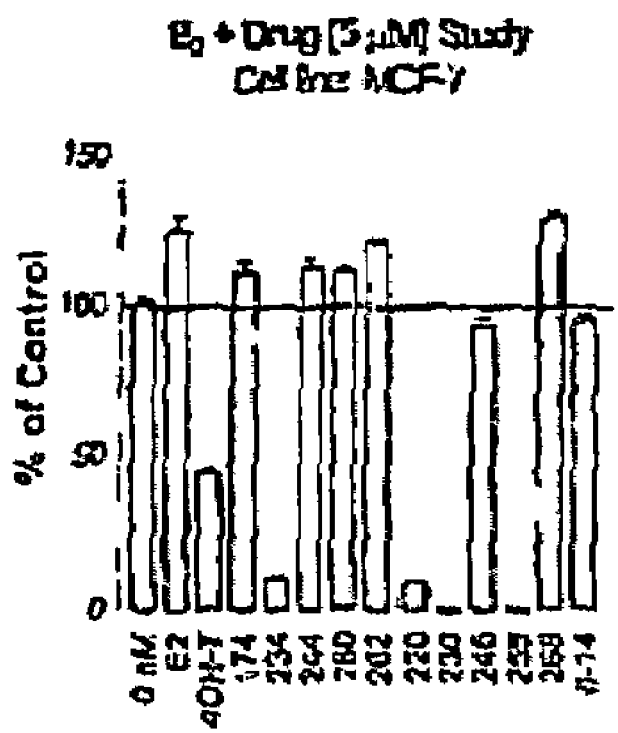
FIG. 7 shows screening data for the isoflavone library (Example 3) in MCF-7 cells in the presence of Estradiol.

Dose response studies were performed with compounds from the combinatorial library. Compounds 234, 220, 244, 230, 258, YWK-II-14 and 4-OH-Tamoxifen were performed. The responses, plotted as Percent of Control versus log [concentration/nM] is shown in FIGS. 5 and 6.

of Estradiol. The results of the screening are shown graphically in FIG. 7.

EXAMPLE 8

Figure 8:
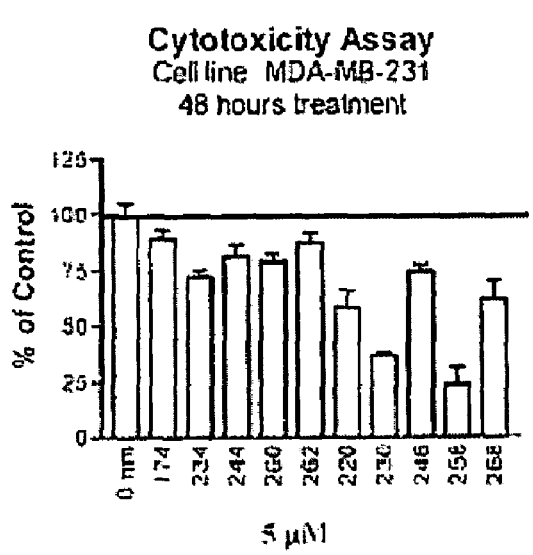
FIG. 8 shows screening data for the isoflavone library (Example 3) in MDA-MB-231 (ER–) cells.
Figure 8:
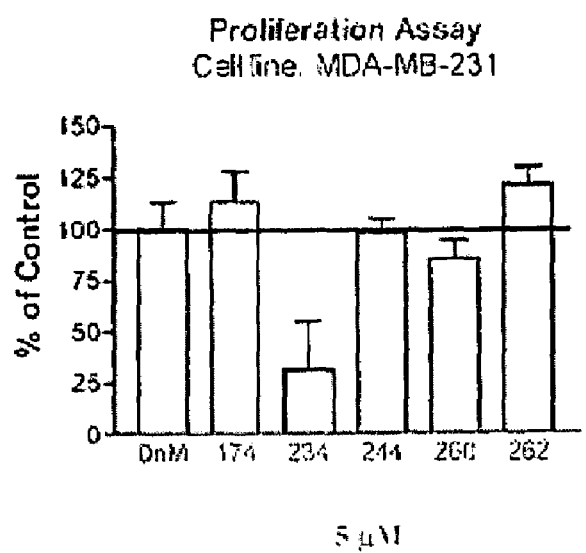

Screening assays for cytotoxicity (2-day) and proliferation (5 day) against the MDA-MB-231 (ER-) cells were preformed. The results are displayed graphically in FIG. 8.

EXAMPLE 9

The following combinatorial compounds were all tested in cell with good activity.

TABLE 3

Compounds tested in Cell, all compounds were soluble in DMSO

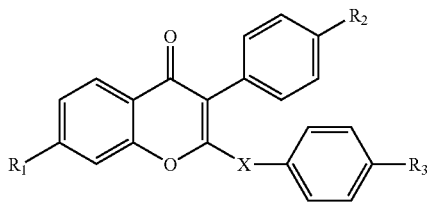

| Compound | X | $R_1$ | $R_2$ | $R_3$ | Mol. Wt. | Amount (mg), 10 µmol each |
|---|---|---|---|---|---|---|
| YWK-I-244 | S | OH | OH | OH | 378.40 | 3.78 |
| YWK-I-260 | S | OH | OH | 2-1-(piperidinyl)ethoxy | 489.58 | 490 |
| YWK-I-234 | S | OH | OMe | 2-1-(piperidinyl)ethoxy | 503.61 | 5.04 |
| YWK-I-268 | O | OH | OH | OH | 362.33 | 3.62 |
| YWK-I-262 | O | OH | OH | 2-1-(piperidinyl)ethoxy | 473.52 | 4.74 |
| YWK-I-272 | O | OH | OMe | 2-1-(piperidinyl)ethoxy | 487.54 | 4.88 |

EXAMPLE 10

The following combinatorial library (compounds 308a–f to 311a–f) was prepared and tested.

TABLE 4

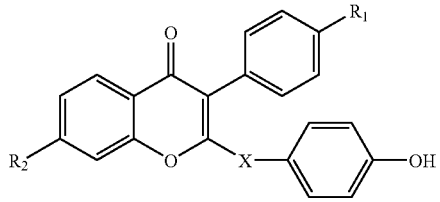

| Compound | X | $R_1$ | $R_2$ | % Yield |
|---|---|---|---|---|
| 308a | S | OMe | OBn | 96 |
| 308b | O | OMe | OBn | 93 |
| 308c | S | H | OMe | 90 |
| 308e | S | Me | OMe | 83 |
| 308f | S | OMe | OMe | 94 |

TABLE 5

| Compound | X | $R_1$ | $R_2$ | % Yield |
|---|---|---|---|---|
| 309a | S | OMe | OBn | 83 |
| 309b | O | OMe | OBn | 89 |
| 309c | S | H | OMe | 84 |
| 309d | S | Me | OMe | 73 |
| 309e | S | OMe | OMe | 78 |

TABLE 6

| Compound | X | $R_1$ | % Yield |
|---|---|---|---|
| 310a | S | OMe | 86 |
| 310b | O | OMe | 87 |
| 310c | S | OH | 93 |
| 310d | O | OH | 92 |
| 310e | S | H | 85 |
| 310f | S | Me | 81 |

TABLE 7

| Compound | X | $R_1$ | % Yield |
|---|---|---|---|
| 311a | S | OMe | 89 |
| 311b | O | OMe | 88 |
| 311c | S | OH | 83 |
| 311d | O | OH | 75 |
| 311e | S | H | 78 |
| 311f | S | Me | 73 |

Figure 9:
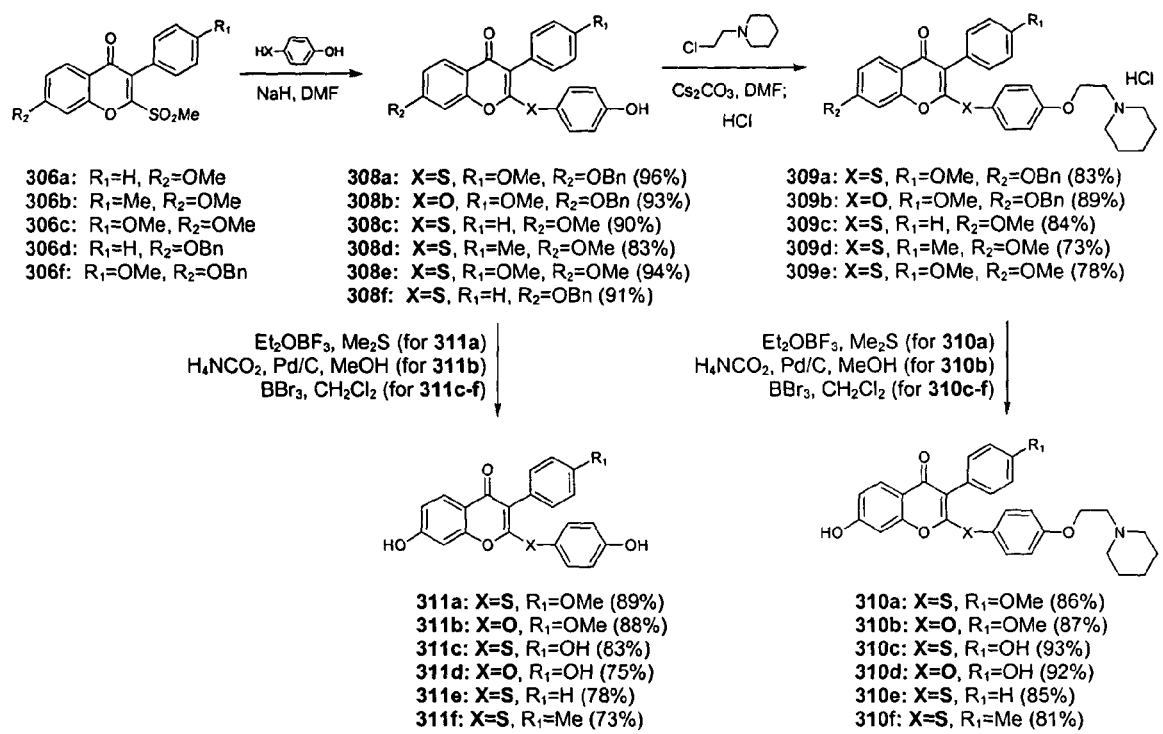
FIG. 9 shows the synthetic scheme for the combinatorial library containing compounds 308a–f, 309a–f, 310a–f, and 311a–f.

Thus, we designed and synthesized several isoflavones containing a basic side chain connected through either an oxygen or a sulfur linkage (synthetic scheme—FIG. 9). Several isoflavones in this series showed potent activities in suppressing proliferation of human breast cancer cell lines, among which compound 310a is the most potent ($IC_{50}$=0.058 µM). Interestingly, however, none of these compounds showed significant binding affinities for ERs, indicating their potent antiproliferative activities might be mediated by other mechanisms.

All documents referenced herein are incorporated by reference.

Although this invention has been described with respect to specific embodiments, the details of these embodiments are not to be construed as limitations.

REFERENCES 1. (a) Cassady, J. M.; Zennie, T. M.; Chae, Y. H. *Cancer Res.* 1988, 48, 6257; (b) Collins, M. B.; Mclachlan, J. A.; Arnold, S. F. *Steroids* 1997, 62, 365; (c) Martin, P. M.; Horowitz, K. B.; Ryan, D. S. *Endocrinology* 1978, 103, 1860; (d) Vrijsen, R.; Everaert, L.; Boeye, A. J. *Gen. Virol.* 1988, 69, 1749; (e) Dickancaite, E.; Nemeikaite, A.; Kalvelyte, A. *Biochem. Mol. Biol. Int.* 1998, 45, 923; (f) Shao, Z. M.; Wu, J.; Shen, Z. Z. *Cell. Biochem.* 1998, 69, 44.
2. (a) Bhat, A. S.; Whetstone, J. L.; Brueggemeier, R. W. *Tetrahedron Lett.* 1999, 40, 2469; (b) Brueggemeier, R. W.; Richards, J. A.; Joomprabutra, S.; Bhat, A. S.; Whetstone, J. L. *J. Steroid Biochem. Mol. Biol.* 2001, 79, 75.
3. (a) Eiden, F.; Schünemann, J. *Arch. Pharm.* (Weinheim) 1985, 318, 1096; (b) Bantick, J. R.; Suschitzky, J. L. *J Heterocyclic Chem.* 1981, 18, 679.
4. Lee, G. H.; Pak, C. S. *Synth. Commun.* 1999, 29, 2539.
5. Lee, A. W. M.; Chan, W. H.; Wong, H. C.; Wong, M. S. *Synth. Commun.* 1989, 19, 547.
6. (a) For the reaction conditions for the synthesis of compounds 5, see: Wähälä, K.; Hase, T. A. *J. Chem. Soc., Perkin Trans.* 1 1991, 3005; (b) Compounds 6a and 6c are commercially available.; (c) Physical and spectral data for compound 6b: mp 71–72° C.; IR (KBr) 1639, 1623, 1516, 1508, 1439, 1388, 1355, 1268, 1231, 1205, 1131 cm$^{-1}$; $^1$H NMR (250 MHz, CDCl$_3$) δ 12.72 (s, 1H), 7.73 (d, J=8.6 Hz, 1H), 7.14–7.24 (m, 4H), 6.43–6.40 (m, 2H), 4.15 (s, 2H), 3.81 (s, 3H), 2.31 (s, 3H); $^{13}$C NMR (62.9 MHz, CDCl$_3$) δ 202.63, 166.56, 166.28, 137.14, 132.47, 131.71, 129.87, 129.61, 113.60, 108.20, 101.43, 55.98, 44.89, 21.48; HRMS calcd for C$_{16}$H$_{16}$NaO$_3$ (M+Na)$^+$ 279.0997, found 279.0989.
7. We have modified the original reaction condition by using THF as an organic solvent instead of carbon disulfide.
8. NMR data for compound 7: $^1$H NMR (400 MHz, CDCl$_3$) δ 6 12.37 (s, 1H), 7.56 (d, J=8.6 Hz, 1H), 7.43–7.45 (m, 2H), 7.27–7.35 (m, 3H), 6.39–6.43 (m, 2H), 3.80 (s, 3H), 2.27 (s, 3H), 2.25 (s, 3H); $^{13}$C NMR (100 MHz, CDCl$_3$) δ 199.21, 166.71, 166.46, 143.82, 137.06, 136.34, 134.11, 129.21, 128.96, 128.83, 113.88, 108.40, 101.43, 56.03, 18.05, 17.28.
9. Physical and spectral data for compounds 2: (a) 2a: mp 140–142° C.; IR (KBr) 1629, 1619, 1584, 1541, 1499, 1431, 1373, 1349, 1252, 1201 cm$^{-1}$; $^1$H NMR (400 MHz, CDCl$_3$) δ 8.13 (d, J=8.9 Hz, 1H), 7.32–7.44 (m, 5H), 6.96 (dd, J=8.9, 2.4 Hz, 1H), 6.84 (d, J=2.3 Hz, 1H), 3.91 (s, 3H), 2.53 (s, 3H); $^{13}$C NMR (62.9 MHz, CDCl$_3$) δ 173.96, 164.41, 164.01, 158.52, 132.64, 131.05, 128.88, 128.68, 128.34, 122.29, 117.66, 114.62, 100.10, 56.30, 14.12; HRMS calcd for C$_{17}$H$_{15}$O$_3$S (M+H)$^+$ 299.0742, found 299.0735. (b) 2b: mp 188–189.5° C.; IR (KBr) 1632, 1612, 1544, 1510, 1433, 1368, 1287, 1265 cm$^{-1}$; $^1$H NMR (400 MHz, CDCl$_3$) δ 8.14 (d, J=8.9 Hz, 1H), 7.20–7.26 (m, 4H), 6.95 (dd, J=8.9, 2.3 Hz, 1H), 6.83 (d, J=2.3 Hz, 1H), 3.90 (s, 3H), 2.53 (s, 3H), 2.37 (s, 3H); $^{13}$C NMR (62.9 MHz, CDCl$_3$) δ 174.08, 164.20, 163.96, 158.51, 138.50, 130.84, 129.68, 129.58, 128.36, 122.24, 117.66, 114.55, 100.08, 56.28, 21.85, 14.14; HRMS calcd for C$_{18}$H$_{16}$NaO$_3$S (M+Na)$^+$ 335.0718, found 335.0721. (c) 2c: mp 169–170° C.; IR (KBr) 1616, 1540, 1437, 1374, 1348, 1252 cm$^{-1}$; $^1$H NMR (400 MHz, CDCl$_3$) δ 8.12 (d, J=8.8 Hz, 1H), 7.24–7.27 (m, 2H), 6.93–6.96 (m, 3H), 6.83 (d, J=2.3 Hz, 1H), 3.90 (s, 3H), 3.82 (s, 3H), 2.52 (s, 3H); $^{13}$C NMR (62.9 MHz, CDCl$_3$) δ 174.15, 164.31, 163.95, 159.90, 158.50, 132.24, 128.32, 124.69, 121.82, 117.61, 114.57, 114.40, 100.07, 56.28, 55.65, 14.15; HRMS calcd for C$_{18}$H$_{16}$NaO$_4$S (M+Na)$^+$ 351.0667, found 351.0668. (d) 2d: mp 117–118° C.; IR (KBr) 1635, 1615, 1585, 1546, 1503, 1435, 1373, 1345, 1252, 1197 cm$^{-1}$; $^1$H NMR (400 MHz, CDCl$_3$) δ 8.13 (d, J=8.9 Hz, 1H), 7.30–7.44 (m, 5H), 6.96 (dd, J=8.9, 2.4 Hz, 1H), 6.81 (d, J=2.3 Hz, 1H), 5.83–5.94 (m, 1H), 5.27 (dd, J=16.9, 1.2 Hz, 1H), 5.14 (dd, J=10.1, 0.8 Hz, 1H), 3.91 (s, 3H), 3.70 (d, J=6.9 Hz, 2H); $^{13}$C NMR (62.9 MHz, CDCl$_3$) δ 174.21, 164.12, 163.40, 158.50, 133.20, 132.61, 131.08, 128.82, 128.68, 128.39, 123.35, 119.27, 117.69, 114.51, 100.13, 56.31, 34.54; HRMS calcd for C$_{19}$H$_{16}$NaO$_3$S (M+Na)$^+$ 347.0718, found 347.0705. (e) 2e: mp 153–154° C.; IR (KBr) 1636, 1617, 1586, 1546, 1502, 1438, 1373, 1341, 1252, 1205 cm$^{-1}$; $^1$H NMR (400 MHz, CDCl$_3$) δ 8.12 (d, J=8.9 Hz, 1H), 7.22–7.41 (m, 10H), 6.95 (dd, J=8.9, 2.4 Hz, 1H), 6.81 (d, J=2.3 Hz, 1H), 4.30 (s, 2H), 3.91 (s, 3H); $^{13}$C NMR (62.9 MHz, CDCl$_3$) δ 174.22, 164.10, 163.54, 158.48, 136.51, 132.52, 131.04, 129.32, 129.17, 128.81, 128.66, 128.39, 128.17, 122.97, 117.70, 114.49, 100.19, 56.31, 36.17; HRMS calcd for C$_{23}$H$_{18}$NaO$_3$S (M+Na)$^+$ 397.0874, found 397.0856.

What is claimed is:

1. A compound of formula A:

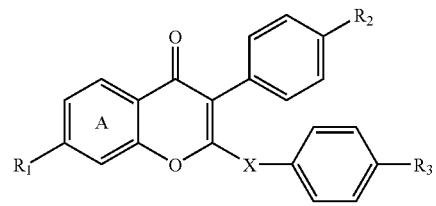

wherein

X is selected from the group consisting of O, N, S, SO, and SO$_2$;

R$_1$ and R$_2$ can be the same or different and are selected from the group consisting of H, OH, OCH$_3$, OCH$_2$CH$_3$, OCH$_2$CH$_5$, NH$_2$, NHCH$_3$, N(CH$_3$)$_2$, CN, CH$_3$, CH$_2$CH$_3$, CH$_2$CH$_2$CH$_3$, CH(CH$_3$)$_2$, C(CH$_3$)$_3$, NO$_2$, F, Cl, Br, CF$_3$, SH, SCH$_3$, SCH$_2$CH$_3$, OCOCH3, OCOC(CH$_3$)$_3$, and OCOCH$_2$COOH;

R$_3$ is

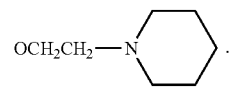

2. A compound of formula A:

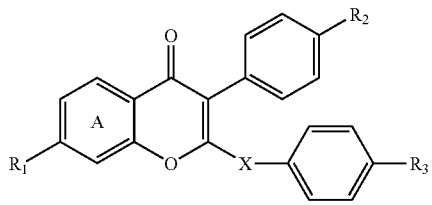

wherein

X is selected from S, N, and O;

$R_1$ and $R_2$ can be the same or different and are selected from the group consisting of H, OH, $OCH_3$, $OCH_2H_3$, $CCH_2C_6H_5$, $NH_2$, $NHCH_3$, $N(CH_3)_2$, CN, $CH_3$, $CH_2CH_3$, $CH_2CH_2CH_3$, $CH(CH_3)_2$, $C(CH_3)_3$, $NO_2$, F, Cl, Br, $CF_3$, SH, $SCH_3$, $SCH_2CH_3$, $OCOCH_3$, $OCOC(CH_3)_3$, and $OCOCH_2COOH$; and $R_3$ is 2-(1-piperidinyl)ethoxy.

3. The compound of claim 2, wherein X is S, $R_1$ is OH, $R_2$ is $OCH_3$, and $R_3$ is 2-(1-piperidinyl)ethoxy.

4. The compound of claim 2 wherein
X is selected from S and O;
$R_1$ is selected from OH, $OCH_3$, and $OC_6H_5$;
$R_2$ is selected from H, OH, $CH_3$, and $OCH_3$; and
$R_3$ is 2-(1-piperidinyl)ethoxy.

5. The compound of claim 2, wherein X is S, $R_1$ is $OC_6H_5$, $R_2$ is $OCH_3$, and $R_3$ is 2-(1-piperidinyl)ethoxy.

6. The compound of claim 2, wherein X is O, $R_1$ is $OC_6H_5$, $R_2$ is $OCH_3$, and $R_3$ is 2-(1-piperidinyl)ethoxy.

7. The compound of claim 2, wherein X is O, $R_1$ is OH, $R_2$ is $OCH_3$, and $R_3$ is 2-(1-piperidinyl)ethoxy.

8. A one-pot method for preparing a 2-(alkylthio)isoflavone comprising the steps of:
    a. providing a mixture of a deoxybenzoin, carbon disulfide, alkyl halide, and tetrabutylammonium hydrogensulfate;
    b. adding aqueous sodium hydroxide to the mixture while stirring;
    c. reacting the mixture until the 2-(alkylthio)isoflavone is formed.

9. The method of claim 8 wherein the mixture is allowed to stir for about 3 to about 7 hours after the addition of the sodium hydroxide.

10. The method of claim 8 further comprising the step of separating the 2-(alkylthio)isoflavone from the reaction mixture.

11. The method of claim 10 further comprising the step of purifying the 2-(alkylthio)isoflavone compound.

12. A method of prepararing a 2-heterosubstituted 3-aryl-4H-benzopyran-4-one compound comprising the steps of:
    a. selecting a 2-(alkylthio)isoflavone;
    b. optionally protecting potentially reactive groups on the 2-(alkylthio)isoflavone;
    c. oxidizing the alkylthio group to a alkylsyfonyl group; and
    d. substituting the alkylsulfonyl group with a heteroalkyl or heteroaryl group to form the 2-heterosubstituted 3-aryl-4H-benzopyran-4-one compound.

13. The method of claim 12 wherein the oxidation step is carried out using mCPBA in a polar aprotic solvent under reflux conditions.

14. The method of claim 12 wherein the polar aprotic solvent is $CH_2Cl_2$.

15. The method of claim 12 wherein alkylsulfonyl group is substituted with a thioaryl group.

16. The method of claim 15 further comprising the step of substituting the thioaryl group with an ethylpiperidinyl group to form a 4-[2-(1-piperidinyl)ethoxy]thiophenyl group at the 2-position of the 2-heterosubstituted 3-aryl-4H-benzopyran-4-one compound.

17. The method of claim 16 further comprising the step of deprotecting the 2-heterosubstituted 3-aryl-4H-benzopyran-4-one.

18. The method of claim 12 further comprising the step of deprotecting the 2-heterosubstituted 3-aryl-4H-benzopyran-4-one.

19. A method for treating, inhibiting, or delaying the onset of a breast cancer in a subject in need of such treatment; the method comprising administering a therapeutically effective amount of compound A:

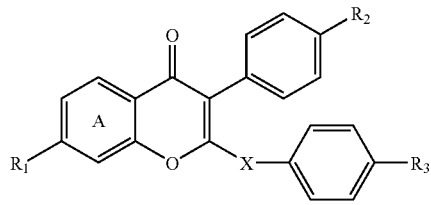

wherein

X is selected from the group consisting of O, N, S, SO, and $SO_2$;

$R_1$ and $R_2$ can be the same or different and are selected from the group consisting of H, OH, $OCH_3$, $OCH_2CH_3$, $OCH_2C_6H_5$, $NH_2$, $NHCH_3$, $N(CH_3)_2$, CN, $CH_3$, $CH_2CH_3$, $CH_2CH_2CH_3$, $CH(CH_3)_2$, $C(CH_3)_3$, $NO_2$, F, Cl, Br, $CF_3$, SH, $SCH_3$, $SCH_2CH_3$, OCOCH3, $OCOC(CH_3)_3$, and $OCOCH_2COOH$; and $R_3$ is 2-(1-piperidinyl)ethoxy to the subject in need of such treatment.

20. The method of claim 19 wherein the cancer is hormone-dependent breast cancer.

* * * * *